United States Patent [19]

Oita

[11] Patent Number: 4,701,252

[45] Date of Patent: Oct. 20, 1987

[54] DISSOLVED GAS AND ION MEASURING ELECTRODE SYSTEM

[75] Inventor: Masahiro Oita, Kashiwara, Japan

[73] Assignee: Matsushita Electric Industrial Co., Ltd., Osaka, Japan

[21] Appl. No.: 906,633

[22] Filed: Sep. 10, 1986

Related U.S. Application Data

[63] Continuation of Ser. No. 504,290, Jun. 14, 1983, abandoned.

[30] Foreign Application Priority Data

Jun. 16, 1982 [JP] Japan .................. 57-104429
Mar. 3, 1983 [JP] Japan .................. 58-35394

[51] Int. Cl.[4] .......................................... G01N 27/46
[52] U.S. Cl. ...................................... 204/402; 204/415
[58] Field of Search ............ 204/402, 409, 415, 416, 204/418, 419, 420, 433, 435; 422/68; 436/68; 128/635; 324/438

[56] References Cited

U.S. PATENT DOCUMENTS

| | | | |
|---|---|---|---|
| 2,995,425 | 8/1961 | Fuhrmann | 422/68 |
| 3,000,805 | 9/1961 | Carritt et al. | 128/635 X |
| 3,155,603 | 11/1964 | Hart | 204/402 |
| 3,496,084 | 2/1970 | Stack, Jr. | 204/402 |
| 3,701,716 | 10/1972 | Deuringer et al. | 204/409 X |
| 3,787,291 | 1/1974 | Deuringer et al. | 204/409 X |
| 3,838,034 | 9/1974 | Groves | 204/409 X |
| 3,875,036 | 4/1975 | Morris et al. | 204/402 |
| 4,003,705 | 1/1977 | Buzza et al. | 436/68 |
| 4,019,861 | 4/1977 | Dahms | 436/68 X |
| 4,060,717 | 11/1977 | Sitek | 204/412 X |
| 4,086,061 | 4/1978 | Hoffa et al. | 422/68 |
| 4,097,921 | 6/1978 | Raffaele | 436/68 X |
| 4,472,261 | 9/1984 | Oita et al. | 204/402 |

FOREIGN PATENT DOCUMENTS 2328921 1/1974 Fed. Rep. of Germany ...... 204/402
2092306 8/1982 United Kingdom .............. 204/402

OTHER PUBLICATIONS

"Glass Electrode Carbon Dioxide Sensor", Beckman Instruments, Inc., Aug. 1960.

Primary Examiner—John F. Niebling
Assistant Examiner—Nam X. Nguyen
Attorney, Agent, or Firm—Wenderoth, Lind & Ponack

[57] ABSTRACT

An automatically depolarizing electrode system for analyzing ions and gases in a solution, especially in blood. A magnetic stirrer is placed in a test chamber of the electrode system and rubs the sensing surface of the electrode which constitutes the wall of the test chamber. During analysis, the rotating stirrer prevents blood from coagulating on the sensing portion of the electrode, so that the electrode is constantly kept clean and depolarized. Preferred is a flat and solid state ion selective electrode for this electrode system. Additionally, the size of the stirrer is designed not only to lessen the amount of a sample solution which is present in the test chamber but to prevent the reading response from retarding.

4 Claims, 6 Drawing Figures

DISSOLVED GAS AND ION MEASURING ELECTRODE SYSTEM

This application is a continuation of now abandoned application Ser. No. 504,290, filed June 14, 1983.

BACKGROUND OF THE INVENTION

1. Field of the Invention

This invention relates to an electrode system for measuring ions and dissolved gases in a solution.

2. Description of the Prior Art

Concentrations of ions and dissolved gases in various industrial waters, including suspensions and solutions in the process of chemical reaction as well, have already been measured and monitored. In clinical fields, too, it has recently become common practice that gases and electrolyte concentrations in blood are measured in order to check the condition of diseases and carry out bedside diagnosis. For example, the analysis of electrolyte in blood is indispensable for diabetics and patients suffering from kidney trouble. In the case of an immature infant requiring respiratory control, excessive oxygen in the blood results in retinitis, and conversely a shortage of oxygen sometimes brings about death or cerebral palsy. Vesicular emphysema and bronchial asthma at times give rise to increase in $pCO_2$ (partial pressure of $CO_2$) in arterial blood and heart failure sometimes results in decrease in $pCO_2$. Sooner or later, importance will be placed in the continuous analysis of arterial blood, especially during an operation. After an operation, too, blood gas analysis is indispensable for checking the condition of a patient who undergoes the operation.

U.S. Pat. No. 2,913,386 discloses an electrolytic device for use in chemical analysis, particularly in a polarographic cell adaptable for use in making quantitative analyses, especially continuous analyses. It covers an electrode pair supported in predetermined spaced relationship and electrically connected by an electrolyte and a selectively permeable barrier for separating the electrode pair and the electrolyte from the composition to be analyzed.

U.S. Pat. No. 3,505,195 discloses an electrode system for electro-chemical measurements of a liquid sample of the type employing at least two electrodes comprising an indicator electrode and a reference electrode. The indicator electrode is vertically disposed in the system and the top surface of the indicator electrode comprises a membrane which defines the bottom wall of the measuring chamber in which the sample is freely accessible from above.

U.S. Pat. No. 3,763,422 discloses a system for determining values of pH, $pCO_2$, and $pO_2$ in a small sample of blood. The system comprises a measuring chamber common to the sensing portions of a flow-through pH electrode, a pH reference electrode, a carbon dioxide ($pCO_2$) electrode, and an oxygen ($pO_2$) electrode. In line and communicating with the chamber exit is a peristaltically activated pump which can drove small samples of blood into the chamber followed by a vacuum system for drawing the sample out of the chamber. Communicating with the chamber entrance is a flush system for cleansing the chamber after the blood has been analyzed.

U.S. Pat. No. 3,732,159 discloses a flow-through sample analyzing chamber in which the electrodes are symmetrically disposed with respect to the fluid inlet and outlet passages, and the chamber construction is such that the flow of fluid therein is symmetrical. A conductive screen may be disposed in the fluid path to provide a uniform electrical field in the vicinity of the active portions of all electrodes.

Concerning glass in use for ion selective electrodes, much work has been done by numerous investigators. Among them U.S. Pat. No. 2,444,845 discloses a glass composition for a pH sensing electrode.

Briefly, little attention has been paid to the structure of the electrode for analyzing fluid such as blood which easily coagulates on the sensing portion of an electrode. The coagulation of blood causes many disadvantages including the response of the electrode to the characteristics of the blood, a poor reproducibility of data, an unstable reading and a short performance life.

SUMMARY OF THE INVENTION

This invention eliminates the above defects and as a result, has enabled an electrode system to automatically depolarize even if a sample such as blood is continuously analyzed for a long period of time.

Therefore, it is a primary object of the present invention to provide an ion and gas measuring electrode system having an automatically depolarizing function which constantly keeps the sensing portion of the electrode clean.

It is another object of the present invention to provide an electrode system carrying out stable reading and having a fast response of measurement for a long period of time.

It is still another object of the present invention to provide an electrode system which makes possible good reproducibility of data.

It is a further object of the present invention to provide an electrode system for saving time and trouble spent on the maintenance of the electrode system.

It is a still further object of the present invention to provide an electrode system for continuous measurement.

It is yet a further object of the present invention to provide an electrode system for flow-through measurement.

It is yet still a further object of the present invention to provide an electrode system for continuous analysis of blood which easily coagulates on the sensing portion of the electrode.

The above and other objects and features of the present invention will appear hereinafter in detail. Specific embodiments of the invention will be shown in the accompanying drawings, in which:

DESCRIPTION OF THE PREFERRED EMBODIMENTS

Figure 1:
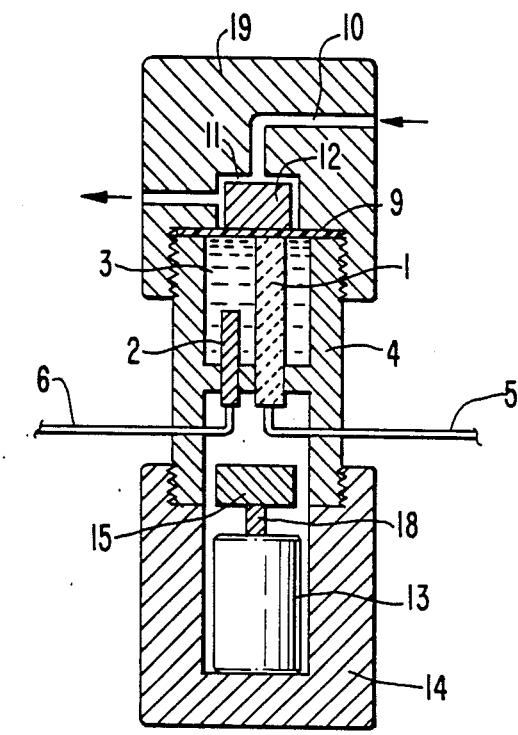
FIG. 1 is a cross-sectional view of an embodiment of a dissolved $CO_2$ gas measuring electrode system having a magnetic stirrer in a test chamber according to the present invention.

A carbon dioxide (pCO₂) electrode system according to the present invention is shown in FIG. 1. A glass electrode 1 used for pH measurement and silver-silver chloride electrode as a reference electrode 2 are disposed in an electrolytic cell 4 which is filled with an electrolyte solution 3 containing sodium hydrogen carbonate. Lead wires 5 and 6 are connected with glass electrode 1 and reference electrode 2, respectively so as to obtain an electric signal from electrodes 1 and 2. The top opening of cell 4 is covered with a gas permeable membrane 9 with the surface of glass electrode 1 pressing against membrane 9. On membrane 9, is mounted a lid 19 having a space for a test chamber 11 which communicates with a channel 10 through which a solution to be analyzed flows. A magnetic stirrer 12 is placed in test chamber 11 and then the bottom of stirrer 12 spontaneously contacts membrane 9 which constitutes the bottom wall of test chamber 11. Magnetic stirrer 12 has usually the shape of a rod or a disk.

Stirrer 12 is coated with resin or glass in order to be prevented from rusting and corroding although it contacts a test solution. On top of that, it is preferable that the surface of stirrer 12 is coated with a polishing agent such as SiC, Al₂O₃, Cr₂O₃ or buffing cloth. Stirrer 12 can conventionally be made of various magnetic materials but a preferred magnetic material for stirrer 12 is rare earth metals having strong magnetism.

All the structural elements are put on a housing 14 in which a motor 13 is installed. A magnet 15 is attached to the shaft 18 of motor 13 for rotating magnetic stirrer 12 placed in test chamber 11. Stirrer 12 which is pulled toward magnet 15 rotates on the sensing portion of membrane 9 against the opposite surface of which glass electrode 1 presses. This pulling strength helps maintain a good contact between stirrer 12 and the sensing portion of membrane 9. When a solution such as blood which is prone to coagulate is analyzed, the rotating stirrer 12 prevents blood from coagulating on membrane 9 or the sensing portion of electrode 1. Accordingly, during continuous measurement of the properties of blood the surface of membrane 9 is kept as clean as it initially was. In other words, the electrode system restores automatically its function and is constantly maintained depolarized.

Unless such a step is taken, the coagulation of blood occurs gradually on membrane 9 until the precipitate of blood plugs the narrow paths in membrane 9 through which CO₂ gas can penetrate. Eventually, the so-called the polarization phenomenon of an electrode system occurs and the system begins to show slow response, unstable reading, and poor reproducibility of data. Under such circumstances, accurate measurement can no longer be carried out, and maintenance including the cleaning of the electrode system and the exchange of membrane 9 is required.

The principle of this pCO₂ electrode system is based on the following reaction (1):

$$CO_2 + H_2O \rightleftharpoons H_2CO_3 \rightleftharpoons H^+ + HCO_3^- \tag{1}$$

wherein CO₂ in a test solution passes through CO₂ gas permeable membrane 9 resulting in a difference of hydrogen ion concentration which is detected by pH glass electrode 1 immersed in a H₂CO₃ containing electrolyte solution 3. Gas permeable membrane 9 may be made, for example, of fluoride resin, polyethylene, polypropylene, or polycarbonate, which allows gas to penetrate through it independently of the perviousness of any solution.

A glass electrode for measuring pH in various industrial waters is per se well-known. A typical glass electrode which is commercially available comprises a glass tube with the bottom of the tube covered with a pH sensing glass film, a silver-silver chloride electrode placed in said tube, an electrolyte solution with which fills said tube, and an upper lid for preventing the electrolyte solution from leaking. The pH sensing glass film is commonly made by rapidly inflating a heated small glass ball which is attached to a glass tube. The production method of the glass electrode is such that the pH sensing glass film has curvature. It is difficult for such a conventional pH glass electrode to be used upside down or tilted because of the presence of electrolyte solution. Moreover, the curved sensing glass film makes it difficult for the magnetic stirrer 12 placed in the test chamber 11 come in close contact with the sensing portion of membrane 9 which is inevitably curved along the glass film. Accordingly, a preferred glass electrode according to the present invention is a solid state electrode, and its sensing portion is flat.

Figure 2:
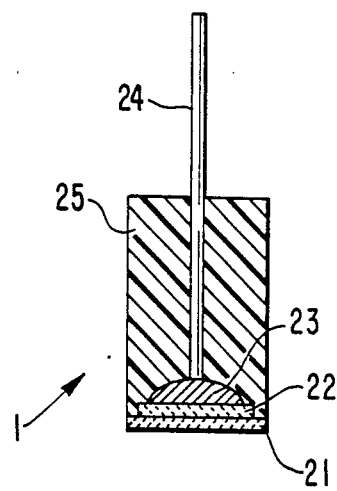
FIG. 2 is a cross-sectional view of an embodiment of a solid state glass electrode according to the present invention.

The structure of a solid state glass electrode is shown in FIG. 2. One example of a glass composition in practical use for a pH electrode is known as 63SiO₂.2-8Li₂O.2Cs₂O.5BaO.2La₂O. The mixture of finely divided powder having the above composition is melted in a platinum crucible at a temperature of 1300° C. for 10 hours and then quickly poured into a mold in order to obtain a glass rod. This rod is cut into a thin glass film 21 having a diameter ranging from 3 mm to 30 mm and a thickness ranging from 50 microns to 500 microns. The central area of one side of glass film 21 is treated with a drop of 10% AgF aqueous solution at a temperature of 40° C. and then dried. This process is repeated several times in succession. After standing for a night the glass film is soaked in 5% LiCl aqueous solution for 20 hours to turn the AgF layer to an AgCl layer 22 which will generate a more stable electric potential. Glass film 21 is cleaned with distilled water, and dried in air, followed by heating at a temperature of 300° C. for 2 hours in an atmosphere such as argon and nitrogen, to settle the AgCl layer 22 on film 21. After that, a lead wire 24 is connected with AgCl layer 22 by using a conductive resin 23 such as Ag-paint. Finally, resin 25 such as epoxy is cast on the treated side of glass film 21 in order to obtain a rod .shaped electrode 1. Before measurement is carried out, it is preferable that the sensing portion of glass film 21 be smoothly polished for stable reading of data.

The above described electrode i.e. solid state glass electrode 1 according to the present invention has the following advantages:

(1) It can be used in any position such as being tilted, horizontal and upside down because no electrolyte solution is used.

(2) It is easy to handle because the thin and fragile glass film is reinforced with resin.

(3) Since the surface of the glass film is ground flat, it is easy for its sensing portion to be in close contact with a stirrer which is placed and rotated in a test chamber.

As described hereinbefore, an electrode system according to the present invention has a channel (10) communicating with test chamber 11 so that flow-through measurement can be easily carried out. When arterial blood is continuously analyzed in vitro, it is advisable to flow blood as slowly as possible in order to minimize the amount of blood required for the continuous analysis. The slow blood flow, however, tends to retard the replacement of blood staying in test chamber 11 and fails to follow an abrupt concentration change.

Figure 3:
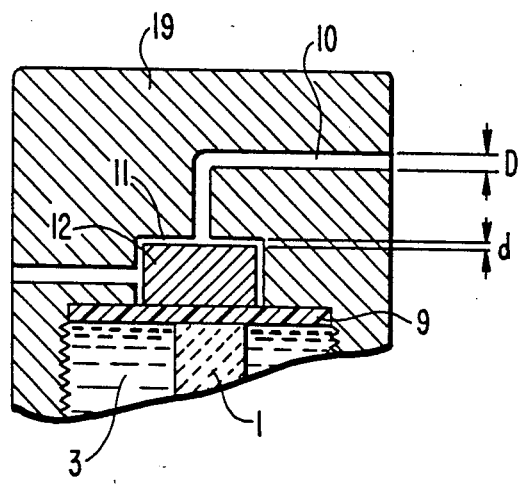
FIG. 3 is an enlarged fragmentary detail cross-sectional view of an embodiment of a $pCO_2$ electrode system showing the relationship between a space in a test chamber having a magnetic stirrer therein and a channel communicating with the test chamber according to the present invention.

Considering the above situation, the relationship between the size of magnetic stirrer 12 which is located in test chamber 11 and the space of test chamber 11 is important. The preferred relationship between them according to the present invention is shown in FIG. 3. The size of stirrer 12 is designed in such a manner that the gap (D) between stirrer 12 and the wall of test chamber 11 opposite the membrane 9 is less than the diameter (d) of channel 10 as expressed in the following formula (2):

$$D > d \tag{2}$$

Figure 4:
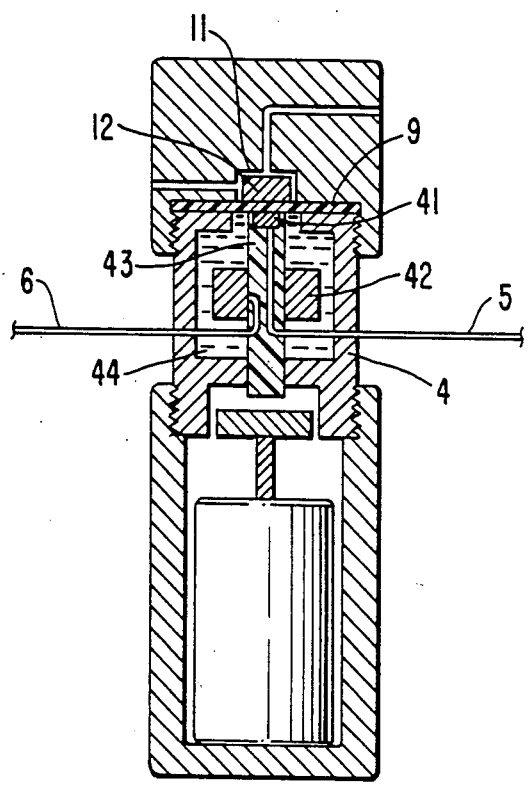
FIG. 4 is a cross-sectional view of an embodiment of a dissolved $O_2$ gas electrode system having a magnetic stirrer in a test chamber according to the present invention.

Next, a dissolved oxygen measuring electrode system according to the present invention is shown in FIG. 4. This electrode system is almost the same as the carbon dioxide electrode system shown in FIG. 1. A precious metal indicator electrode 41 made of a material such as gold or platinum is mounted on the end surface of a plastic rod 43. A ring shaped Ag/AgCl electrode 42 which serves as a reference electrode 42 is mounted on the side surface of rod 43 so as to surround rod 43. Electrode rod 43 is attached to a bottom opening of an electrolytic cell 4 and immersed in an electrolytic solution 44 such as a phosphate buffer solution.

This electrode works as follows. Since a predetermined electrolytic voltage ranging from 0.4 volt to 0.8 volt is applied between indicator electrode 41 and reference electrode 42 through leads 5 and 6, oxygen gas passed through membrane 9 reaches indicator electrode 41 and decomposes according to the following reaction (3):

$$O_2 + 2H_2O + 4e^- \rightarrow 4OH^- \tag{3}$$

This produces a polarographic current proportional to the oxygen concentration of the solution being analyzed.

In the case of the $pCO_2$ electrode system, the effect of magnetic stirrer 12 provided in test chamber 11 has already been described. The same is true in the $pO_2$ electrode system in terms of preventing blood from coagulating the sensing surface of membrane 9 against the opposite surface of which indicator electrode 41 presses. Thus, in this case, too, long performance life, stable reading and good reproducibility of data are obtained and as the result, continuous analysis of blood can be carried out.

Figure 5:
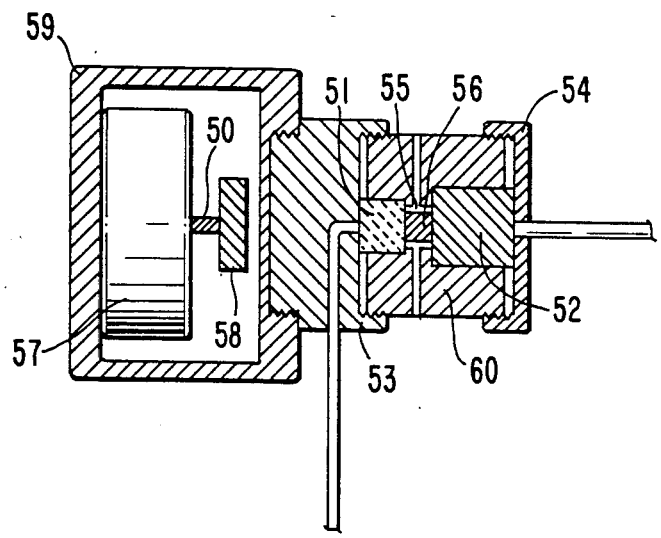
FIG. 5 is a cross-sectional view of an embodiment of a pH electrode system wherein the electrodes of an electrode pair consisting of a pH sensing glass electrode and a reference electrode face each other and constitute the wall of the test chamber having a magnetic stirrer therein according to the present invention.

Next, a vertical cross-sectional view of a pH electrode system is shown in FIG. 5. An electrode pair consisting of a glass electrode 51 for pH measurement and a reference electrode 52 is inserted in an electrolytic cell 60 into opposite side openings of cell 60 so as to face each other. Stoppers 53 and 54 are used to fix the two electrodes 51 and 52, respectively, in place and a space formed between the sensing portions of electrodes 51 and 52 constitutes a test chamber 55. A magnetic stirrer 56 according to the present invention is placed in test chamber 55 and rotated by an external magnet 58 attached to a shaft 50 of a motor 57 which is installed in housing 59.

Since the sensing portions of the electrode pair 51 and 52 are rubbed by only the one stirrer 56 at the same time, they are constantly kept as clean as they originally were. When two surfaces of the electrode pair are polished with one stirrer as in the above case, priority should be given to pH glass electrode 51 because the pH glass electrode is more easily influenced by any contamination than reference electrode 52. Namely, external magnet 58 should be disposed near glass electrode 51 so as to pull stirrer 56 in the direction of glass electrode 51. This allows stirrer 56 to come in closer contact with glass electrode 51 than reference electrode 52.

Glass electrode 51 employed in this pH measuring electrode system is also a solid state electrode. As described hereinbefore, a flat sensing portion can be easily obtained in the solid state electrode. This ground flat sensing portion of electrode 51 may help remove precipitate such as coagulated blood and proteins in blood from the sensing portion thereof because of resultant close contact between stirrer 56 placed in test chamber 55 and the sensing portion thereof.

By using the above described electrode according to the present invention, it is easily understood that not merely stable reading of measurement values but long performance life, and good reproducibility of data as well are successfully achieved.

Figure 6:
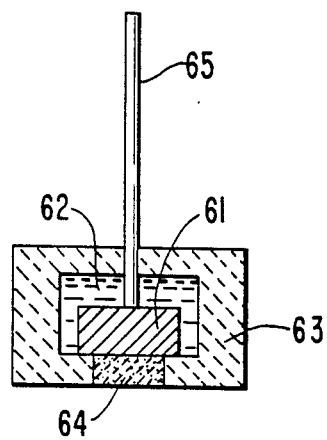
FIG. 6 is a cross-sectional view of an embodiment of a reference electrode according to the present invention.

One example of the reference electrode according to the present invention is shown in FIG. 6. An Ag/AgCl electrode 61 having a lead 65 is placed in a glass or plastic vessel 63 filled with KCl aqueous solution as an electrolyte solution 62. The bottom wall of vessel 63 has a liquid junction 64 of a material such as porous glass, ceramics and resin. Otherwise, it is also possible to prepare a pinhole in the bottom wall in place of liquid junction 64. Instead of an Ag/AgCl electrode 61, a satulated calomel electrode which is commercially available can also be employed.

As far as pNa, pK, and pCl electrode systems are concerned, they are obtained by using their respective glass or ceramic electrodes in place of a pH sensing glass electrode in the to pH electrode system shown in FIG. 5. The compositions of sensing materials of such electrodes are quite different from each other, but a method for making solid state electrodes from them is the same as described hereinbefore in the case of the pH glass electrode. A typical example of the glass composition of pNa electrode is $71SiO_2 \cdot 18Al_2O_3 \cdot 11Na_2O$ and glass having a composition of $70SiO_2 \cdot 3Al_2O_3 \cdot 27Na_2O$ is popular for a pK electrode. On the other hand, a ceramic electrode is commonly used for a pCl electrode. It is produced in such a manner that a composition comprising AgCl (50~80 wt %) and AgS (50~20 wt %) is baked at a temperature ranging from 180° C. to 250° C. while being pressed. If a $pCO_2$ electrode and a $pO_2$ electrode are used in place of a pH electrode and a reference electrode, respectively in the electrode system shown in FIG. 5, an electrode system for simultaneous determination of $CO_2$ and $O_2$ is easily obtained.

The electrode systems hereinbefore described are not restricted only to vertical use. They can be used in a position in which they are tilted, horizontal and upside down.

Various modifications and additions may be made to the above described electrode systems without departing from the scope of the present invention. Accordingly, the invention disclosed hereinbefore shall be interpreted in an illustrative and not in a limiting sense.

What is claimed is:

1. An electrode system for measuring dissolved gas and ions in a solution, comprising:

a pair of electrodes consisting of a measuring electrode and a reference electrode and each having a flat sensing surface, said sensing surfaces being in spaced opposed relation;

a test chamber having opposite walls constituted by the flat sensing surfaces of said pair of electrodes;

a magnetic stirrer and rubbing body consisting of a block of magnetic material having flat surfaces on opposite sides thereof and positioned in said test chamber between said electrodes with said flat surfaces in sliding contact with the flat surfaces of said electrodes so as to rub simultaneously said sensing surfaces of said electrodes; and means positioned outside said test chamber and directly magnetically coupled with said magnetic stirrer and rubbing body for rotating said magnetic stirrer and rubbing body so that said sensing surface is rubbed by said magnetic stirrer and rubbing body.

2. An electrode system according to claim 1 wherein said measuring electrode is a $pO_2$ gas electrode.

3. An electrode system according to the claim 1 wherein said measuring electrode is a $pCO_2$ gas electrode.

4. An electrode system according to claim 1 wherein said measuring electrode is an ion selective electrode.

* * * * *